US009637769B2

(12) United States Patent
Škulj et al.

(10) Patent No.: US 9,637,769 B2
(45) Date of Patent: May 2, 2017

(54) REDUCTION OF FORMATION OF AMIDATED AMINO ACIDS IN CELL LINES FOR PROTEIN EXPRESSION

(71) Applicant: LEK PHARMACEUTICALS D.D., Ljubljana (SI)

(72) Inventors: Mihaela Škulj, Menges (SI); Dominik Gaser, Menges (SI)

(73) Assignee: LEK PHARMACEUTICALS D.D. (SI)

( * ) Notice: Subject to any disclaimer, the term of this patent is extended or adjusted under 35 U.S.C. 154(b) by 13 days.

(21) Appl. No.: 14/384,803

(22) PCT Filed: Apr. 16, 2013

(86) PCT No.: PCT/EP2013/057866
§ 371 (c)(1),
(2) Date: Sep. 12, 2014

(87) PCT Pub. No.: WO2013/156458
PCT Pub. Date: Oct. 24, 2013

(65) Prior Publication Data
US 2015/0079634 A1 Mar. 19, 2015

(30) Foreign Application Priority Data
Apr. 16, 2012 (EP) ..................... 12164264

(51) Int. Cl.
| | | |
|---|---|---|
| C12N 15/00 | (2006.01) | |
| C12P 21/00 | (2006.01) | |
| C12N 15/113 | (2010.01) | |
| C12P 21/02 | (2006.01) | |
| C12N 9/02 | (2006.01) | |

(52) U.S. Cl.
CPC ............ *C12P 21/00* (2013.01); *C12N 9/0071* (2013.01); *C12N 15/1137* (2013.01); *C12P 21/02* (2013.01); *C12Y 114/17003* (2013.01); *C12N 2310/14* (2013.01)

(58) Field of Classification Search
CPC .......... C12N 15/00; C12N 15/85; C12P 21/00
See application file for complete search history.

(56) References Cited

FOREIGN PATENT DOCUMENTS

| | | |
|---|---|---|
| WO | WO 2006/084111 | 8/2006 |
| WO | WO-2007/087253 A2 | 8/2007 |
| WO | WO 2012/062810 | 5/2012 |
| WO | WO 2013/156458 | 10/2013 |

OTHER PUBLICATIONS

Farrell. 2010; Biosynthesis of fatty acid amides. Graduate Theses and Dissertations at scholarcommons.usf.edu/etd/1629; pp. 1 and 192-197.*

Kolhekar et al. 2002; Essential features of the catalytic core of peptidyl-alpha-hydroxyglycine alpha-amidating lyase. Biochemistry. 41: 12384-12394.*

Czyzyk et al. 2005; Deletion of peptide amidation enzymatic activity leads to edema and embryonic lethality in mouse. Developmental Biology. 287: 301-313.*

Office Action issued on Apr. 1, 2016 by the Korean Intellectual Property Office for application KR 10-2014-7031609, filed on Nov. 11, 2014 (Applicant—LEK Pharm., D.D.) (English Translation—6 pages).

Patent Examination Report No. 1 issued on Mar. 3, 2016 by the Australian Intellectual Property Office for application AU 2013248356, filed on Apr. 16, 2013 (Applicant—LEK Pharm. D.D.) (4 pages).

Office Action issued on Feb. 10, 2016 by the Canadian Intellectual Property Office for application CA 2,864,466, filed on Apr. 16, 2013 (Applicant—LEK Pharm., D.D.) (4 pages).

Bradbury, A. F., et. al., "4-Phenyl-3-butenoic acid, and in vivo inhibitor of peptidylglycine hydroxylase (peptide amidating enzyme);" *European Journal of Biochemistry*, 189: 363-368 (1990).

Cermak, T., et al., "Efficient design and assembly of custom TALEN and other TAL effector-based constructs for DNA targeting," *Nucl. Acids Res.* 39(12) (2011).

Iwai, N., et. al., "Autocrine growth loops dependent on peptidyl α-amidating enzyme as targets for novel tumor cell growth inhibitors," *Lung Cancer*, 23: 209-222 (1999).

Mains, R. E., et. al., Inhibition of peptide amidation by disulfiram and diethyldithiocarbainate, *The Journal of Biological Chemistry*, 261: 11938-11941 (1986).

Najvirtova, M., et. al., "A role of thyrotropin-releasing hormone in insulin secretion by isolated rat pancreatic islets," *European Journal of Physiology*, 449: 547-552 (2005).

Prigge, S. T., et. al., "Amidation of bioactive peptides: the structure of peptidylglycine alpha-hydroxylating monooxygenase" *Science*, 278: 1300-1305 (1997).

Santiago, Y., et al., "Targeted gene knockout in mammalian cells by using engineered zinc-finger nucleases," *PNAS*, Apr. 15, 2008, vol. 105, No. 15 (2008).

Sunman, J. A., et. al., "Reversal of the transformed phenotype and inhibition of peptidylglycine α-monooxygenase in Ras-transformed cells by 4-Phenyl-3-Butenoic Acid," *Molecular Carcinogenesis*, 41: 231-246 (2004).

Walsh, G., et al., "Post-translational modifications in the context of therapeutic Proteins," *Nature Biotechnology*, 24: 1241-1252 (2006).

International Search Report mailed on Aug. 26, 2013 for International Patent Application PCT/EP2013/057866, which was filed Apr. 16, 2013 and published as WO 2013/156458 on Oct. 24, 2013 (Applicant: Lek Pharmaceuticals D.D.// Inventor: Mihaela Škulj) (pp. 1-6).

International Preliminary Report on Patentability issued on Oct. 21, 2014 for International Application No. PCT/EP2013/057866, which was filed on Apr. 16, 2013 and published as WO 2013/156458 on Oct. 24, 2013. (Applicant: LEK Pharmaceuticals D.D.// Inventor: Mihaela Škulj) (pp. 1-11).

Written Opinion dated Oct. 16, 2014 for International Patent Application PCT/EP2013/057866, which was filed Apr. 16, 2013 and published as WO 2013/156458 on Oct. 24, 2013 (Applicant: Lek Pharmaceuticals D.D.// Inventor: Mihaela Škulj) (pp. 1-9).

(Continued)

*Primary Examiner* — Karen Cochrane Carlson
(74) *Attorney, Agent, or Firm* — Ballard Spahr LLP

(57) ABSTRACT

The present invention is related to a method to reduce peptide amidation activity in a given cell line, cell lines with reduced peptide amidation activity, and uses thereof.

24 Claims, 5 Drawing Sheets

(56) References Cited

OTHER PUBLICATIONS

Figure 1:
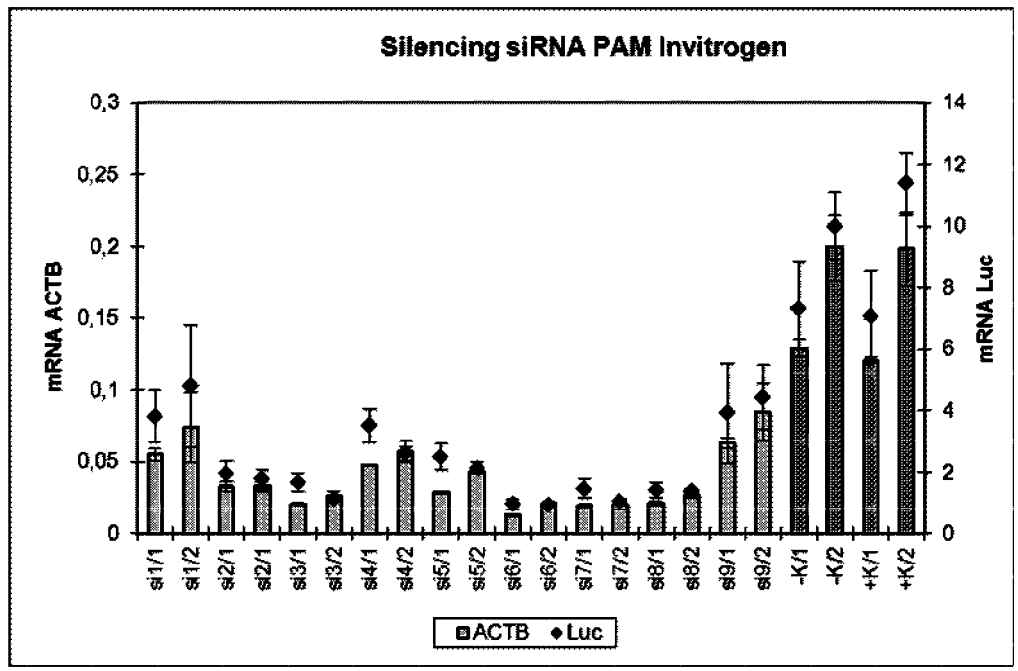

Patent Examination Report No. 2 issued on Jul. 18, 2016 by the Australian Intellectual Property Office for application AU 2013248356, filed on Apr. 16, 2013 (Applicant—LEK Pharm. D.D.) (4 pages).

Morgan, et al., "Uncovering the Biosynthetic Pathway of Oleamide," FASEB Journal, 2006, vol. 20, No. 5, pp. A949-A950.

Yonekura, et al., "Identification of the Five Essential Histidine Residues for Peptidyglycine Monooxygenase," Biochemical and Biophysical Research Communications, 1996, vol. 218, pp. 495-499.

Notice of Reasons for Rejection issued by the JPO on Aug. 9, 2016 for application JP 2015-506206, filed on Apr. 16, 2013 and published as JP 2015-519884 on Jul. 16, 2015 (Applicant—Retsuku Pharma) (Original—6 pages // English Translation—9 pages).

\* cited by examiner

SEQUENCE LISTING

<160> NUMBER OF SEQ ID NOS: 31

<210> SEQ ID NO 1
<211> LENGTH: 672
<212> TYPE: DNA

-continued

<213> ORGANISM: Cricetulus griseus

<400> SEQUENCE: 1

```
gggagtgctc ctaagccagg ccagttcagt gttcctcaca gtttggccct tgtgcctcat    60
ttggaccagt tgtgtgtggc agacagggaa aatggccgga tccaatgttt cagaactgac   120
accaaagaat ttgtgagaga gattaaacat gcgtcatttg ggagaaatgt attcgcaatt   180
tcatatatat caggtttgct ctttgcagta aatgggaagc cttactttgg agaccatgaa   240
cctgtgcaag gctttgtgat gaacttttcc agtggggaaa ttatagatgt cttcaagcca   300
gtacgcaagc actttgacat gcctcacgat gtggttgcct ctgacgatgg gaatgtgtac   360
attggagacg cacacacgaa cacggtgtgg aagttcaccc tgactgaaaa aatggagcat   420
cgatcggtta aaaaggcagg cattgaggct caggaaatca agaaaccga ggcagttgtt    480
gaatccaaaa tggagaacaa acccacctcc tcagaattgc agaagatgca agagaaacag   540
aaactgatca agagccaggt tcgggagtg cccgtggttc tcattacaac ccttctggtt   600
attcctgtgg ttgtcctgct ggccattgtc atgtttattc ggtggaaaaa atcaagggcc   660
tttggaggaa aa                                                       672
```

<210> SEQ ID NO 2
<211> LENGTH: 25
<212> TYPE: RNA
<213> ORGANISM: Artificial Sequence
<220> FEATURE:
<223> OTHER INFORMATION: siRNA_1

<400> SEQUENCE: 2

```
caguugugug uggcagacag ggaaa                                          25
```

<210> SEQ ID NO 3
<211> LENGTH: 25
<212> TYPE: RNA
<213> ORGANISM: Artificial Sequence
<220> FEATURE:
<223> OTHER INFORMATION: siRNA_2

<400> SEQUENCE: 3

```
cggauccaau guuucagaac ugaca                                          25
```

<210> SEQ ID NO 4
<211> LENGTH: 25
<212> TYPE: RNA
<213> ORGANISM: Artificial Sequence
<220> FEATURE:
<223> OTHER INFORMATION: siRNA_3

<400> SEQUENCE: 4

```
ccaauguuuc agaacugaca ccaaa                                          25
```

<210> SEQ ID NO 5
<211> LENGTH: 25
<212> TYPE: RNA
<213> ORGANISM: Artificial Sequence
<220> FEATURE:
<223> OTHER INFORMATION: siRNA_4

<400> SEQUENCE: 5

```
gagagagauu aaacaugcgu cauuu                                          25
```

<210> SEQ ID NO 6
<211> LENGTH: 25

```
<212> TYPE: RNA
<213> ORGANISM: Artificial Sequence
<220> FEATURE:
<223> OTHER INFORMATION: siRNA_5

<400> SEQUENCE: 6
caugcgucau uugggagaaa uguau                                              25

<210> SEQ ID NO 7
<211> LENGTH: 25
<212> TYPE: RNA
<213> ORGANISM: Artificial Sequence
<220> FEATURE:
<223> OTHER INFORMATION: siRNA_6

<400> SEQUENCE: 7
ugggagaaau guauucgcaa uuuca                                              25

<210> SEQ ID NO 8
<211> LENGTH: 25
<212> TYPE: RNA
<213> ORGANISM: Artificial Sequence
<220> FEATURE:
<223> OTHER INFORMATION: siRNA_7

<400> SEQUENCE: 8
gggagaaaug uauucgcaau ucau                                               25

<210> SEQ ID NO 9
<211> LENGTH: 25
<212> TYPE: RNA
<213> ORGANISM: Artificial Sequence
<220> FEATURE:
<223> OTHER INFORMATION: siRNA_8

<400> SEQUENCE: 9
cacacgaaca cgguguggaa guuca                                              25

<210> SEQ ID NO 10
<211> LENGTH: 25
<212> TYPE: RNA
<213> ORGANISM: Artificial Sequence
<220> FEATURE:
<223> OTHER INFORMATION: siRNA_9

<400> SEQUENCE: 10
caaagaaacc gaggcaguug uugaa                                              25

<210> SEQ ID NO 11
<211> LENGTH: 21
<212> TYPE: DNA
<213> ORGANISM: Artificial Sequence
<220> FEATURE:
<223> OTHER INFORMATION: siRNA_1

<400> SEQUENCE: 11
caguaaaugg gaagccuuat t                                                  21

<210> SEQ ID NO 12
<211> LENGTH: 21
<212> TYPE: DNA
<213> ORGANISM: Artificial Sequence
<220> FEATURE:
<223> OTHER INFORMATION: siRNA_2

<400> SEQUENCE: 12
```
aggcaguugu ugaauccaat t                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA_3

<400> SEQUENCE: 13
aacagaaacu gaucaaagat t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA_4

<400> SEQUENCE: 14
caagagaaac agaaacugat t                                              21

<210> SEQ ID NO 15
<211> LENGTH: 21
<212> TYPE: DNA
<213> ORGANISM: Artificial Sequence
<220> FEATURE:
<223> OTHER INFORMATION: siRNA_5

<400> SEQUENCE: 15
gaacugacac caaagaauut t                                              21

<210> SEQ ID NO 16
<211> LENGTH: 21
<212> TYPE: DNA
<213> ORGANISM: Artificial Sequence
<220> FEATURE:
<223> OTHER INFORMATION: siRNA_6

<400> SEQUENCE: 16
uuucagaacu gacaccaaat t                                              21

<210> SEQ ID NO 17
<211> LENGTH: 65
<212> TYPE: DNA
<213> ORGANISM: Artificial Sequence
<220> FEATURE:
<223> OTHER INFORMATION: SH5_HLPAM

<400> SEQUENCE: 17
gatccgaact gacaccaaag aattctcaag agaaattctt tggtgtcagt tctgtttttt    60
ggaaa                                                                65

<210> SEQ ID NO 18
<211> LENGTH: 66
<212> TYPE: DNA
<213> ORGANISM: Artificial Sequence
<220> FEATURE:
<223> OTHER INFORMATION: SH6_HLPAM

<400> SEQUENCE: 18
gatccgtttc agaactgaca ccaaactcaa gagatttggt gtcagttctg aaacattttt    60
tggaaa                                                               66

<210> SEQ ID NO 19
<211> LENGTH: 65
<212> TYPE: DNA
<213> ORGANISM: Artificial Sequence
<220> FEATURE:
<223> OTHER INFORMATION: shRNA_Bottom Strand Oligonucleotide

<400> SEQUENCE: 19
agcttttcca aaaacagaa ctgacaccaa agaatttctc ttgagaattc tttggtgtca    60
gttcg                                                              65

<210> SEQ ID NO 20
<211> LENGTH: 66
<212> TYPE: DNA
<213> ORGANISM: Artificial Sequence
<220> FEATURE:
<223> OTHER INFORMATION: shRNA_Bottom Strand Oligonucleotide SH6_HLPAM

<400> SEQUENCE: 20
agcttttcca aaaatgttt cagaactgac accaaatctc ttgagtttgg tgtcagttct    60
gaaacg                                                             66

<210> SEQ ID NO 21
<211> LENGTH: 18
<212> TYPE: DNA
<213> ORGANISM: Artificial Sequence
<220> FEATURE:
<223> OTHER INFORMATION: Forward sequencing primer

<400> SEQUENCE: 21
aggcgattaa gttgggta                                                18

<210> SEQ ID NO 22
<211> LENGTH: 20
<212> TYPE: DNA
<213> ORGANISM: Artificial Sequence
<220> FEATURE:
<223> OTHER INFORMATION: Reverse sequencing primer

<400> SEQUENCE: 22
taatacgact cactataggg                                              20

<210> SEQ ID NO 23
<211> LENGTH: 22
<212> TYPE: DNA
<213> ORGANISM: Artificial Sequence
<220> FEATURE:
<223> OTHER INFORMATION: Forward primer PAM

<400> SEQUENCE: 23
ggccggatcc aatgtttcag aa                                           22

<210> SEQ ID NO 24
<211> LENGTH: 16
<212> TYPE: DNA
<213> ORGANISM: Artificial Sequence
<220> FEATURE:
<223> OTHER INFORMATION: Forward primer ACTB

<400> SEQUENCE: 24
agccacgctc ggtcag                                                  16

<210> SEQ ID NO 25
<211> LENGTH: 23
<212> TYPE: DNA

```
<213> ORGANISM: Artificial Sequence
<220> FEATURE:
<223> OTHER INFORMATION: Forward primer LUC

<400> SEQUENCE: 25 ctgattttc ttgcgtcgag ttt                                              23

<210> SEQ ID NO 26
<211> LENGTH: 26
<212> TYPE: DNA
<213> ORGANISM: Artificial Sequence
<220> FEATURE:
<223> OTHER INFORMATION: Reverse primer PAM

<400> SEQUENCE: 26
tcccaaatga cgcatgttta atctct                                          26

<210> SEQ ID NO 27
<211> LENGTH: 18
<212> TYPE: DNA
<213> ORGANISM: Artificial Sequence
<220> FEATURE:
<223> OTHER INFORMATION: Reverse primer ACTB

<400> SEQUENCE: 27
catcctgcgt ctggacct                                                   18

<210> SEQ ID NO 28
<211> LENGTH: 24
<212> TYPE: DNA
<213> ORGANISM: Artificial Sequence
<220> FEATURE:
<223> OTHER INFORMATION: Reverse primer LUC

<400> SEQUENCE: 28
gagttgtgtt tgtggacgaa gtac                                            24

<210> SEQ ID NO 29
<211> LENGTH: 17
<212> TYPE: DNA
<213> ORGANISM: Artificial Sequence
<220> FEATURE:
<223> OTHER INFORMATION: Probe PAM

<400> SEQUENCE: 29
ctgacaccaa agaattt                                                    17

<210> SEQ ID NO 30
<211> LENGTH: 17
<212> TYPE: DNA
<213> ORGANISM: Artificial Sequence
<220> FEATURE:
<223> OTHER INFORMATION: Probe ACTB

<400> SEQUENCE: 30
ccgggacctg acagact                                                    17

<210> SEQ ID NO 31
<211> LENGTH: 17
<212> TYPE: DNA
<213> ORGANISM: Artificial Sequence
```

```
<220> FEATURE:
<223> OTHER INFORMATION: Probe LUC

<400> SEQUENCE: 31
tccggtaaga cctttcg                                                    17
```

REDUCTION OF FORMATION OF AMIDATED AMINO ACIDS IN CELL LINES FOR PROTEIN EXPRESSION

CROSS-REFERENCE TO RELATED APPLICATIONS

The present application is a National Phase Application of International Application No. PCT/EP2013/057866, filed Apr. 16, 2013, which claims priority to European Application No. 12164264.9, filed Apr. 16, 2012, which applications are incorporated herein fully by this reference.

REFERENCE TO SEQUENCE LISTING

The Sequence Listing submitted Sep. 11, 2014 as a text file named "13318_0019U1_Sequence_Listing," created on Sep. 11, 2014, and having a size of 7,234 bytes is hereby incorporated by reference pursuant to 37 C.F.R. §1.52(e)(5).

The present invention is related to the reduction of formation of amidated amino acids in cell lines for protein expression.

Although proteins are mainly characterised by their amino acid sequence (primary structure), other aspects, like post-translational modifications, contribute to the characteristics of a protein as well, for example by affecting secondary, tertiary and quaternary structure. Some of these post-translational modifications play a significant role for later protein activity, including safety and efficacy of biopharmaceutical drugs.

One major aspect for the heterogeneity of proteins is the charge pattern including acidic variants, formed, for example, by deamidation of amino acids like asparagine, by glycosylation or by processing of N-terminal glutamine to pyroglutamate, and basic variants, with, for example, amidated amino acids, particularly C-terminal proline amide residues.

The formation of amidated amino acids, like C-terminal proline amide, is however unwanted in some cases, e.g., as a source of undesired heterogeneity, or in case said variants potentially affect protein activity or immunogenicity, or when the amount of amidated amino acids, e.g., proline amide, in the protein which is to be produced is higher, or lower, than in a reference protein.

In contrast to small molecular drugs, which are being produced under highly controllable physico-chemical conditions, the production of proteins, particularly proteins used as biotherapeutics (biopharmaceuticals), is a highly complex matter which is difficult to control, as the production makes use of a living cell culture system. Therefore, it is important to have at hand a toolbox which allows to control particularly post-translational modifications of the proteins produced, in order to be able to provide a constant product quality and a constant high yield, to increase the efficiency of the production process, to increase and/or fine tune the physiological activity of the protein produced and the safety of the derived drug, and/or to match the post-translational features of a produced protein to those of a reference protein.

It is the object of the present invention to provide means and methods which address these needs.

The object is met with methods and means according to the independent claims of the present invention. The dependent claims are related to preferred embodiments. It is to be understood that value ranges delimited by numerical values are to be understood to include the said delimiting values.

SUMMARY OF THE INVENTION

Before the invention is described in detail, it is to be understood that this invention is not limited to the particular component parts of the devices or means described, or process steps of the methods described, as such devices or means and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values.

According to a first aspect of the present invention, a cell for protein expression is provided which has reduced peptide amidation activity.

As used herein, the term "cell" shall also encompass cell lines derived therefrom. Further, animals obtained from such cells or cell lines, cell-based expression platforms shall be covered by the protection provided by such term.

As used herein, the term "for protein expression" implies that the cell according to the invention is suitable for protein expression in an industrial process. This includes both homologous and/or heterologous protein expression. The fact that the cell according to the invention is suitable for protein expression in an industrial process means that cells occurring in a natural environment, which by their nature have reduced peptide amidation activity, but are, as such, and without further modification, isolation or treatment, not suitable for protein expression in an industrial process, if existent, do not anticipate the novelty of the cells according to the present invention.

Peptide amidation is a widespread, often essential post-translational modification undergone by many bioactive peptides. Peptide amidation serves, for example, to catalyse neuroendocrine peptides to active α-amidated products.

Peptide amidation is however unwanted in some cases, e.g., as a source of undesired heterogeneity, or in case said variants potentially affect protein activity or immunogenicity, or when the amount of amidated amino acids, e.g., proline amide, in the protein which is to be produced is higher, or lower, than in a reference protein.

In a preferred embodiment of the cell according to the invention, the reduced peptide amidation activity has been achieved by
a) inhibition or reduction of gene expression of a gene coding for an enzyme catalysing peptide α-amidation;
b) expression of a dysfunctional, or inactive enzyme catalysing peptide α-amidation, or an enzyme catalysing peptide amidation with reduced activity; and/or
c) inhibition or reduction of the activity of an enzyme catalysing peptide α-amidation.

According to another aspect of the invention, a method to reduce peptide amidation activity in a given cell is provided, which method comprises at least one step selected from the group consisting of
a) inhibition or reduction of gene expression of a gene coding for an enzyme catalysing peptide α-amidation;
b) expression of a dysfunctional, or inactive enzyme catalysing peptide α-amidation, or an enzyme catalysing peptide amidation with reduced activity; and/or
c) inhibition or reduction of the activity of an enzyme catalysing peptide α-amidation.

According to a preferred embodiment of the invention, the reduced peptide amidation activity has been, or can be, achieved by at least one step selected from the group consisting of
  gene silencing,
  gene knock-down,
  gene knock-out,
  delivery of a dominant negative construct,
  conditional gene knock-out, and/or
  gene alteration
with respect to a gene coding for an enzyme catalysing peptide α-amidation.

The term "gene expression", as used herein, is meant to encompass at least one step selected from the group consisting of DNA transcription into mRNA, mRNA processing, non-coding mRNA maturation, mRNA export, translation, protein folding and/or protein transport.

The inhibition or reduction of gene expression of a gene refers to methods which directly interfere with gene expression, encompassing, but not restricted to, inhibition or reduction of DNA transcription, e.g., by use of specific promoter-related repressors, by site specific mutagenesis of a given promoter, by promoter exchange, or inhibition or reduction of translation, e.g., by RNAi induced post-transcriptional gene silencing.

The expression of a dysfunctional, or inactive enzyme catalysing peptide α-amidation, or an enzyme catalysing peptide amidation with reduced activity, can, for example, be achieved by site specific or random mutagenesis, insertions or deletions within the coding gene.

The inhibition or reduction of the activity of an enzyme catalysing peptide amidation can, for example, be achieved by administration of, or incubation with, an inhibitor to the respective enzyme, prior to or simultaneously with protein expression. Examples for such inhibitors include, but are not limited to, an inhibitory peptide, an antibody, an aptamer, a fusion protein or an antibody mimetic against said enzyme, or a ligand or receptor thereof, or an inhibitory peptide or nucleic acid, or a small molecule with similar binding activity.

Other ways to inhibit the enzyme are the reduction of specific cofactors of the enzyme in the medium, like copper, which is a PAM specific ion cofactor (e.g., in the form of $CuSO_4$), ascorbate, which acts as an electron donor for PAM, molecular oxygen, catalase and others known today to the skilled artisan, or yet to be discovered in the future.

Gene silencing, gene knock-down and gene knock-out refers to techniques by which the expression of a gene is reduced, either through genetic modification or by treatment with an oligonucleotide with a sequence complementary to either an mRNA transcript or a gene. If genetic modification of DNA is done, the result is a knock-down or knock-out organism. If the change in gene expression is caused by an oligonucleotide binding to an mRNA or temporarily binding to a gene, this results in a temporary change in gene expression without modification of the chromosomal DNA and is referred to as a transient knock-down.

In a transient knock-down, which is also encompassed by the above term, the binding of this oligonucleotide to the active gene or its transcripts causes decreased expression through blocking of transcription (in the case of gene-binding), degradation of the mRNA transcript (e.g. by small interfering RNA (siRNA) or RNase-H dependent antisense) or blocking either mRNA translation, pre-mRNA splicing sites or nuclease cleavage sites used for maturation of other functional RNAs such as miRNA (e.g., by Morpholino oligos or other RNase-H independent antisense). Other approaches involve the use of shRNA (small hairpin RNA, which is a sequence of RNA that makes a tight hairpin turn that can be used to silence gene expression via RNA interference), esiRNA (Endoribonuclease-prepared siRNAs, which are a mixture of siRNA oligos resulting from cleavage of long double-stranded RNA (dsRNA) with an endoribonuclease), or the activation of the RNA-induced silencing complex (RISC).

Other approaches to carry out gene silencing, knock-down or knock-out are known to the skilled person from the respective literature, and their application in the context of the present invention is considered as routine.

Gene knock-out refers to techniques by which the expression of a gene is fully blocked, i.e. the respective gene is inoperative, or even removed. Methodological approaches to achieve this goal are manifold and known to the skilled person. Examples are the production of a mutant which is dominantly negative for the given gene. Such mutant can be produced by site directed mutagenesis (e.g., deletion, partial deletion, insertion or nucleic acid substitution), by use of suitable transposons, or by other approaches which are known to the skilled person from the respective literature, the application of which in the context of the present invention is thus considered as routine. One example for a newly developed technique which the skilled person would consider as useful in the context of the present invention is knock-out by use of targeted Zinc Finger Nucleases. A respective Kit is provided by Sigma Aldrich as "CompoZR knockout ZFN". Another approach encompasses the use of Transcription activator-like effector nucleases (TALENs).

The delivery of a dominant negative construct involves the introduction of a sequence coding for a dysfunctional enzyme, e.g., by transfection. Said coding sequence is functionally coupled to a strong promoter, in such way that the gene expression of the dysfunctional enzyme overrules the natural expression of the wild type enzyme, which, in turn, leads to an effective physiological defect of the respective enzyme activity.

A conditional gene knock-out allows to block gene expression in a tissue- or time-specific manner. This is done, for example, by introducing short sequences called loxP sites around the gene of interest. Again, other approaches are known to the skilled person from the respective literature, and their application in the context of the present invention is considered as routine.

One other approach is gene alteration which may lead to a dysfunctional gene product or to a gene product with reduced activity. This approach involves the introduction of frame shift mutations, nonsense mutations (i.e., introduction of a premature stop codon) or mutations which lead to an amino acid substitution which renders the whole gene product dysfunctional, or causing a reduced activity. Such gene alteration can for example be produced by mutagenesis (e.g., deletion, partial deletion, insertion or nucleic acid substitution), either unspecific (random) mutagenesis or site directed mutagenesis.

Protocols describing the practical application of gene silencing, gene knock-down, gene knock-out, delivery of a dominant negative construct, conditional gene knock-out, and/or gene alteration are commonly available to the skilled artisan, and are within his routine. The technical teaching provided herein is thus entirely enabled with respect to all conceivable methods leading to an inhibition or reduction of gene expression of a gene coding for an enzyme catalysing peptide α-amidation, or to the expression of a dysfunctional, or inactive enzyme catalysing peptide α-amidation, or an enzyme catalysing peptide amidation with reduced activity.

According to another preferred embodiment of the invention, the cell is a eukaryotic cell. The term "eukaryotic cell"

encompasses, but is not restricted to, animal cells, like, e.g., insect cells, plant cells and fungal cells. Accordingly, a preferred embodiment of the invention provides that the cell is an animal cell and/or a plant cell.

According to yet another preferred embodiment of the invention, the cell is a mammalian cell. According to still another preferred embodiment of the invention, the cell is at least one selected from the group consisting of:

Baby hamster Kidney cells (e.g., BHK21)
Chinese hamster ovary cells (e.g., CHO-K1, CHO-DG44, CHO-DXB, or CHO-dhfr$^-$)
Mouse myeloma cells (e.g., SP2/0 or NS0)
Human embryonic kidney cells (e.g., HEK-293)
Human-retina-derived cells (e.g., PER-C6), and/or
Amniocyte cells (e.g., CAP).

According to another preferred embodiment, the cell is a recombinant cell. As used herein, the term "recombinant cell" is used to refer to a cell with exogenous and/or heterologous nucleic acid incorporated within, either incorporated stably so as to remain incorporated in clonal expansion of the cells, or introduced transiently into a cell (or a population of cells). Such exogenous and/or heterologous nucleic acid can either code for a heterologous protein to be expressed, or it can effect the inhibition or reduction of gene expression of a gene coding for an enzyme catalysing peptide α-amidation, or the expression of a dysfunctional or inactive enzyme catalysing peptide α-amidation, or an enzyme catalysing peptide amidation with reduced activity.

Preferably, the enzyme catalysing peptide amidation is a peptidylglycine alpha-amidating monooxygenase (PAM). PAM is a multifunctional protein containing two enzymatic activities that act sequentially to catalyse the C-terminal truncation and alpha-amidation of peptides. Peptidylglycine alpha-hydroxylating monooxygenase (PHM) catalyses the first step of the reaction and is dependent on copper (Cu), or copper ions, ascorbate, and molecular oxygen. The zinc dependent peptidylamido-glycolate lyase (PAL) catalyses the second step of the reaction, the amidation of the now C-terminal proline to proline amide. For a reaction scheme of the process catalysed by both enzymes see FIG. 9. The actual gene or enzyme is of course dependent on the cell which is used for protein expression.

One example for such gene or enzyme is human peptidylglycine alpha-amidating monooxygenase (Gene ID according to the NCBI Gene database: 5066), the gene of which encodes a multifunctional protein which has two enzymatically active domains with catalytic activities: (i) peptidylglycine alpha-hydroxylating monooxygenase (PHM) and (ii) peptidyl-alpha-hydroxyglycine alpha-amidating lyase (PAL). These catalytic domains work sequentially to catalyse neuroendocrine peptides to active alpha-amidated products. Multiple alternatively spliced transcript variants encoding different isoforms have been described for this gene but some of their full length sequences are not yet known. The gene is located on 5q14-q21. In case the cell used for protein expression is a human cell (e.g., HEK, PER-C6 or CAP), it is preferably provided that (i) the gene expression of said gene is inhibited or reduced, or that (ii) a dysfunctional or inactive enzyme, or an enzyme with reduced activity, is expressed, or that (iii) the activity of said enzyme is inhibited or reduced.

Another example for such gene or enzyme is peptidylglycine alpha-amidating monooxygenase of hamsters, like the Chinese hamster (*Cricetulus griseus*), from which CHO cells (Chinese hamster ovary cells) can be derived. The respective gene sequence is not yet published in public databases, although proprietary databases exist in which respective expression sequence tags (ESTs) are listed.

In case the cell used for protein expression is a hamster cell (e.g., BHK or CHO or CAP), it is preferably provided that (i) the gene expression of said gene is inhibited or reduced, or that (ii) a dysfunctional or inactive enzyme, or an enzyme with reduced activity, is expressed, or that (iii) the activity of said enzyme is inhibited or reduced.

Another example for such gene or enzyme is murine peptidylglycine alpha-amidating monooxygenase (Gene ID: 18484), the gene of which encodes a multifunctional protein which has two enzymatically active domains with catalytic activities: (i) peptidylglycine alpha-hydroxylating monooxygenase (PHM) and (ii) peptidyl-alpha-hydroxyglycine alpha-amidating lyase (PAL). These catalytic domains work sequentially to catalyse neuroendocrine peptides to active alpha-amidated products. Multiple alternatively spliced transcript variants encoding different isoforms have been described for this gene but some of their full length sequences are not yet known. The gene is located on 1D; 1 57.5 cM.

In case the cell used for protein expression is a mouse cell (e.g., SP2/0 or NS0) it is preferably provided that (i) the gene expression of said gene is inhibited or reduced, or that (ii) a dysfunctional or inactive enzyme, or an enzyme with reduced activity, is expressed, or that (iii) the activity of said enzyme is inhibited or reduced.

Other examples comprise insect peptidylglycine alpha-amidating monooxygenase COOH-terminal interactor protein-1 (gene IDs are for example 5567876, 6053618 or 6043293) in case the cell used for protein expression is an insect cell.

Peptidylglycine alpha-amidating monooxygenase present in other potential cells for protein expression (like in yeasts, plants, filamentous fungi, or even bacteria) shall also be encompassed by the scope of the present invention. Likewise, other enzymes capable of peptide amidation, particularly capable of proline amide formation, shall also be encompassed by the scope of the present invention. The transfer of the teaching of the present invention to these enzymes does not involve any additional inventive step.

The cell or method according to any of the aforementioned aspects and embodiments of the present invention, wherein the gene expression of the gene coding for said enzyme catalysing peptide amidation is inhibited, or reduced, by means of RNA interference (RNAi).

RNAi is an RNA-dependent gene silencing process that is controlled by the RNA-induced silencing complex (RISC) and is initiated by short double-stranded RNA molecules in a cell's cytoplasm, where they interact with the catalytic RISC component Argonaut. The RNAi pathway is found in many eukaryotes including animals and is initiated by the enzyme Dicer, which cleaves long double-stranded RNA (dsRNA) molecules into short fragments of ~20 nucleotides that are called siRNAs. Each siRNA is unwound into two single-stranded ssRNAs, namely the passenger strand and the guide strand. The passenger strand will be degraded, and the guide strand is incorporated into the RNA-induced silencing complex.

For gene silencing purposes in genetic engineering, the RNA is imported directly into the cytoplasm and cleaved to short fragments by the enzyme. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus and then exported to the cytoplasm to be cleaved by Dicer. Thus, the two dsRNA pathways, exogenous and endogenous, converge at the RISC complex.

Preferably, long double-stranded RNAs (dsRNAs; typically >200 nt) are used to silence the expression of the gene coding for said enzyme catalysing peptide α-amidation. Upon introduction, the dsRNAs is cleaved into 20-25 nucleotide small interfering RNAs (siRNAs) by Dicer (initiation step). Then, the siRNAs assemble into RISCs, unwinding in the process.

The siRNA strands subsequently guide the RISCs to complementary RNA molecules, where they cleave and destroy the cognate RNA (effecter step). Cleavage of cognate RNA takes place near the middle of the region bound by the siRNA strand. In mammalian cultured cells, RNAi is typically induced by the use of siRNAs. There are two general methods for producing siRNAs in cultured cells: delivery of synthetic siRNAs, and introduction of a DNA construct that expresses short hairpin RNA sequences (shRNA) that are processed to siRNAs within the cell. The respective siRNAs and shRNAs used in the context of the present invention are shown in the experimental section.

If the RNA interference (RNAi) leads to a non-transient inhibition of gene expression which can be established in the respective cell line also in next generation cells, the result is a knock down or knock out cell or cell line.

According to still another preferred embodiment of the invention, the enzyme catalysing peptide amidation catalyses the formation of C-terminal proline amide residues The heavy chain of many human immunoglobulins has, on its C-terminal (e.g., in the constant region), a sequence motif consisting of -Pro-Gly-Lys-COOH (one letter code: PGK), wherein the C-terminal Lys is frequently subject of removal by basic carboxypeptidases, thus leaving -Pro-Gly-COOH at the C-terminus.

Figure 9:
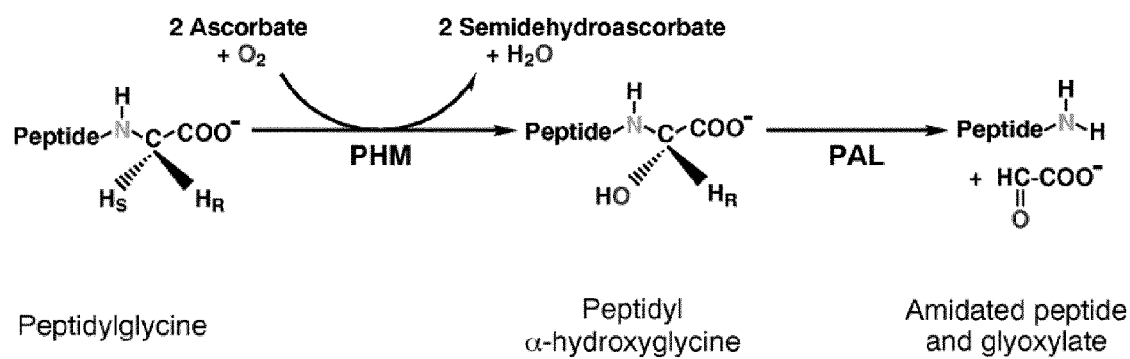

In many protein expression systems, this sequence motif is the target of enzymes catalysing peptide α-amidation, like peptidylglycine alpha-amidating monooxygenase, which for example converts the C-terminal peptidyl-prolyl-glycine into peptidyl-prolyl-α-hydrooxiglycine, and then into peptidyl-prolin-α-amide and glyoxylate (see FIG. 9 and respective description).

The formation of C-terminal proline amide residues is thus frequently seen in the protein expression of monoclonal antibodies and derivatives thereof comprising a heavy chain constant region, like IgG, receptor-immunoglobulin fusion proteins having an Fc region of human immunoglobulin, like etanercept or aflibercept, or immunotoxins and trifunctional antibody having an Fc region.

According to another aspect of the invention, the use of a cell according to any of the aforementioned claims for homologous protein expression is provided.

According to yet another aspect of the invention, the use of a cell according to any of the aforementioned claims for heterologous protein expression is provided.

The term "heterologous protein expression", as used herein, shall refer to the protein expression of a gene, a nucleic acid or a cDNA, which is foreign to the cell in which the expression occurs ("host cell", or "expression system"). Heterologous (meaning 'derived from a different organism') refers to the fact that often the transferred protein was initially cloned from or derived from a different cell type or a different species, and coding genetic material (e.g., "cDNA") was obtained which is then transferred to the host cell. The genetic material that is transferred typically must be within a format that encourages the recipient cell to express the cDNA as a protein (i.e., it is part of an expression vector). Methods for transferring foreign genetic material into a recipient cell include transfection and transduction. The choice of recipient cell type is often based on an experimental need to examine the protein's function in detail, and the most prevalent recipients, known as heterologous expression systems, are chosen, among others, for (i) ease of transfer DNA, (ii) capability of creating the protein in a pharmaceutically efficacious form, function, (iii) protein yield, and the like.

The term "recombinant protein expression" largely overlaps with the term "heterologous protein expression" The term "recombinant" alludes to the fact that "new" (coding) genetic material has been introduced into an expression system, e.g., a cell. Such process results in the formation of a recombinant nucleic acid (e.g., a recombinant DNA), and the host is thus called a recombinant host, e.g., a recombinant cell. One idea behind this process is to produce a protein from one organism (e.g., a human protein) in another organism, e.g., in a cell-based protein expression system, like a CHO cell.

Preferably, said protein is at least one protein selected from the group consisting of:
an antibody, or a fragment or derivative thereof
a fusion protein,
an antibody mimetic, and/or
non-antibody proteins.

The term "antibody", as used herein, shall relate to immunoglobulins, or fragments or derivatives thereof. Particularly preferred, such antibody is selected from the group consisting of IgG, IgD, IgE, IgA and/or IgM, or a fragment or derivative thereof. As used herein, the term "fragment" shall refer to fragments of such antibody retaining, in some cases, target binding capacities, e.g.
a CDR (complementarity determining region)
a hypervariable region,
a variable domain (Fv)
an IgG heavy chain (consisting of VH, CH1, hinge, CH2 and CH3 regions)
an IgG light chain (consisting of VL and CL regions), and/or
a Fab and/or F(ab)$_2$ As used herein, the term "derivative" shall refer to protein constructs being structurally different from, but still having some structural relationship to, the common antibody concept, e.g., scFv, as well as bi-, tri- or higher specific antibody constructs, antibody-based fusion proteins, antibody-drug conjugates, immunotoxins and the like.

The term "antibody mimetic" relates to a non-immunoglobulin-based target-binding protein molecule. Such antibody mimetics are for example derived from ankyrin repeat proteins, C-type lectins, A-domain proteins of *Staphylococcus aureus*, transferrins, lipocalins, fibronectins, Kunitz domain protease inhibitors, ubiquitin, cysteine knots or knottins, thioredoxin A, and so forth, and are known to the skilled person in the art from the respective literature.

The term "fusion protein", as used herein, shall primarily relate to receptor-immunoglobulin fusion proteins having, e.g., an Fc region of human immunoglobulin.

Preferably, the cells and methods according to the present invention are suitable for the (recombinant) production of proteins comprising amino acid sequences identical to or substantially similar to all or part of one of the following proteins: an Flt3 ligand, a CD40 ligand, erythropoiesis stimulating proteins like erythropoietin (EPO), darbepoetin including darbepoetin alfa, and thrombopoietin, calcitonin, leptin, a Fas ligand, a ligand for receptor activator of NF-kappa B (RANKL), a tumour necrosis factor (TNF)- related apoptosis-inducing ligand (TRAIL), thymic stroma-derived lymphopoietin, granulocyte colony stimulating factor, granulocyte-macrophage colony stimulating factor (GM-CSF), growth factors including mast cell growth factor, stem cell growth factor, epidermal growth factor, keratinocyte growth factor, megakaryote growth and development factor, RANTES, growth hormone, insulin, insulinotropin, insulin-like growth factors, parathyroid hormone, interferons including α-interferon, β-interferon, and γ-interferon, nerve growth factor, brain-derived neurotrophic factor, synaptotagmin-like proteins (SLP1-5), neurotrophin-3"glucagon, interleukins including IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, and IL-18, colony stimulating factors, lymphotoxin-p, tumour necrosis factor (TNF), leukemia inhibitory factor, oncostatin-M, and various ligands for cell surface molecules ELK and Hek (such as the ligands for eph-related kinases or LERKS).

Further proteins that can be produced using the methods and means of the invention include proteins comprising all or part of the amino acid sequence of a receptor for any of the above-mentioned proteins, an antagonist to such a receptor of any of the above-mentioned proteins, and proteins substantially similar to such receptors or antagonists.

Also, proteins that can be produced using the methods and means of the invention include proteins comprising all or part of the amino acid sequences of differentiation antigens (referred to as CD proteins) or their ligands or proteins substantially similar to either of these. Examples of such antigens are differentiation antigens including CD20, CD22, CD27, CD30, CD39, CD40, and ligands thereto.

Enzymatically active proteins or their ligands can also be produced using the methods and means of the invention. Examples include proteins comprising all or part of one of the following proteins, or their ligands, or proteins substantially similar to one of these: metalloproteinase-disintegrin family members, kinases, glucocerebrosidase, superoxide dismutase, tissue plasminogen activator, Factor VIII, Factor IX, apolipoprotein E, apolipoprotein A-1, globins, an IL-2 antagonist, alpha-1 antitrypsin, TNF-alpha Converting Enzyme, ligands for any of the above-mentioned enzymes, and numerous other enzymes and their ligands.

Disclaimer

The particular combinations of elements and features in the above detailed embodiments are exemplary only; the interchanging and substitution of these teachings with other teachings in this application are also expressly contemplated. As those skilled in the art will recognise, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

BRIEF DESCRIPTION OF THE EXAMPLES AND DRAWINGS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

DRAWINGS

In all figures, error bars show standard deviation. All shown results were further analysed with Student's T-test (see below).

FIG. 1: Silencing of PAM mRNA using siRNA (Invitrogen) on CHO K1 PD cells. /1: parallel 1, /2: parallel 2, −K: nontransfected CHO K1 PD cells, +K: CHO K1 PD cells transfected with scrambled siRNA (Ambion).

Figure 2:
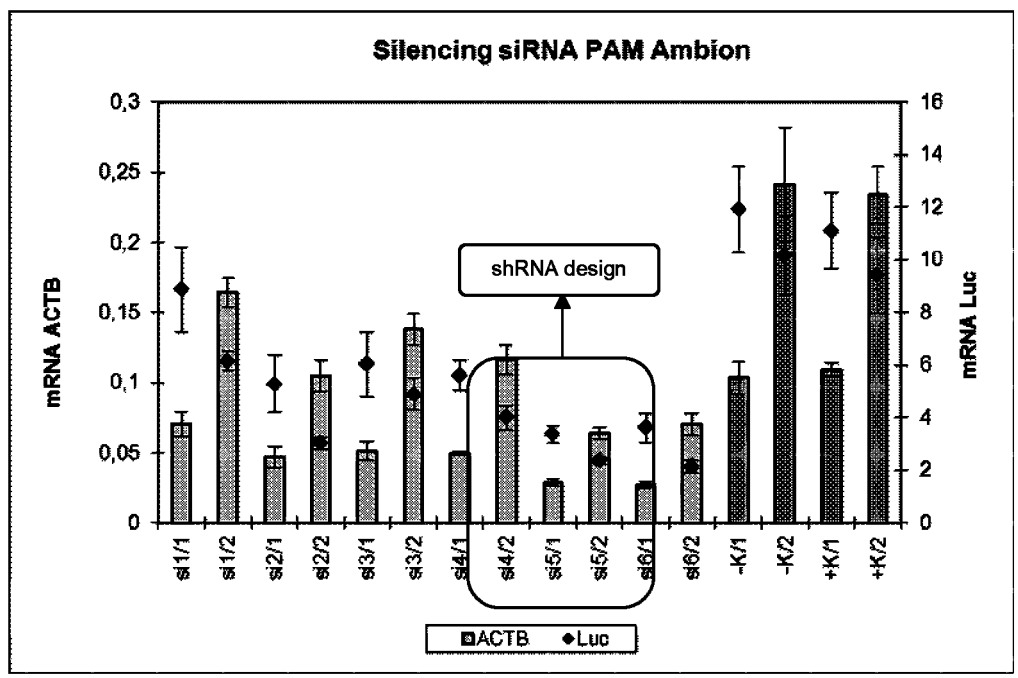

FIG. 2: Silencing of PAM mRNA using siRNA (Ambion) on CHO K1 PD cells. /1: parallel 1, /2: parallel 2, −K: nontransfected CHO K1 PD cells, +K: CHO K1 PD cells transfected with scrambled siRNA (Ambion).

The experiments shown in FIGS. 1 and 2 were designed to evaluate the silencing effect on the PAM gene by siRNA provided by Invitrogen or Ambion. CHO K1 PD cells were transfected by siRNAs to determine the sequence with the most potent silencing effect. This was also proven by calculating % decrease in expression of PAM mRNA (Table 9) and using Student's t-Test (Table 10).

Figure 3:
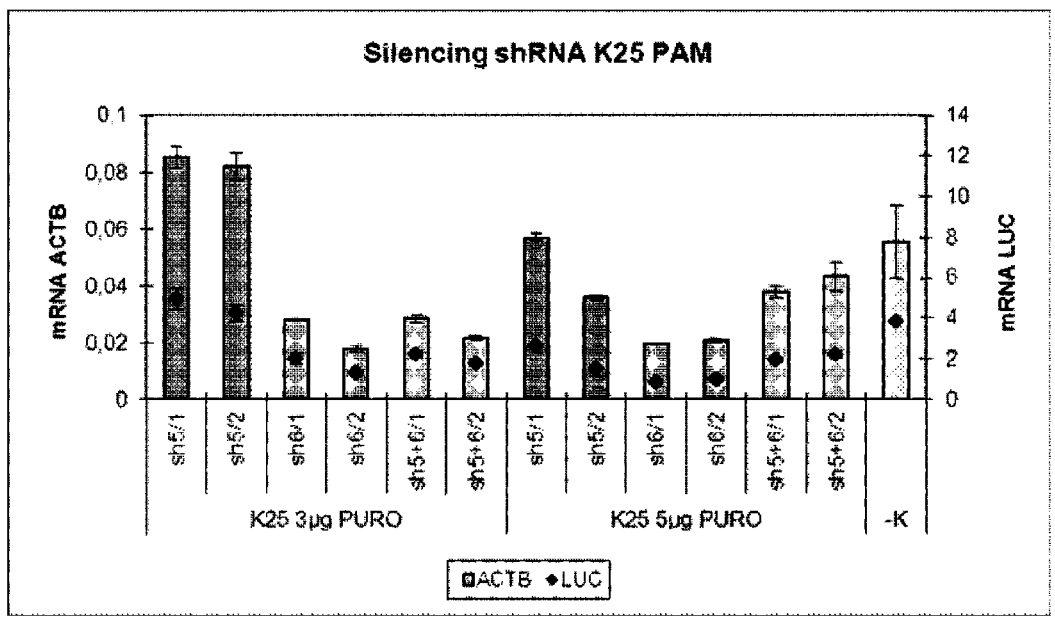

FIG. 3: Silencing of PAM mRNA using shRNA on clone K25. /1: parallel 1, /2: parallel 2, −K: nontransfected K25 cells.

Figure 4:
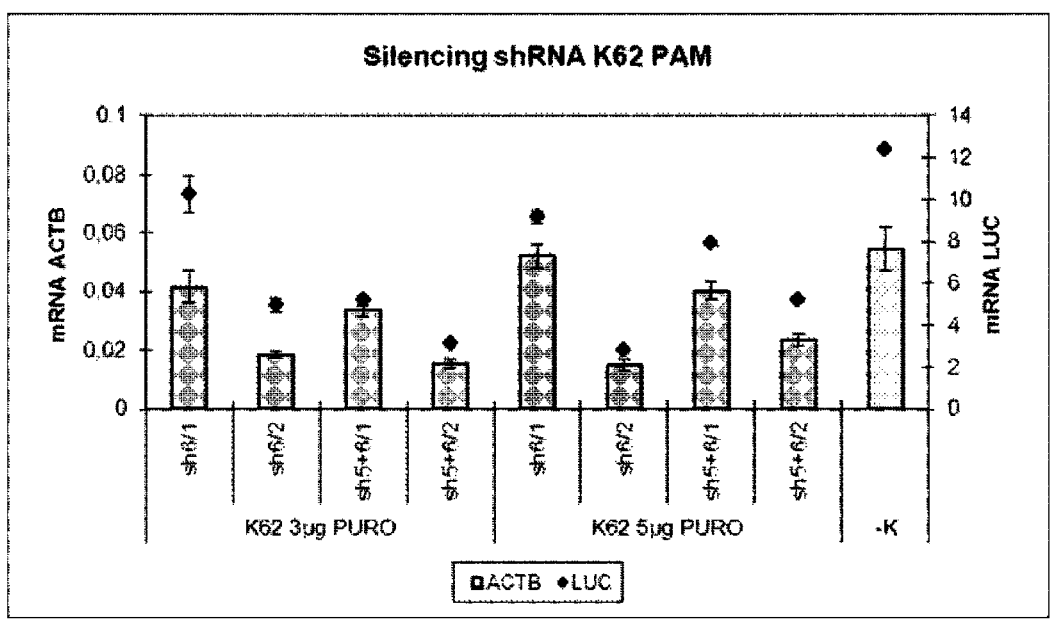

FIG. 4: Silencing of PAM mRNA using shRNA on clone K62. /1: parallel 1, /2: parallel 2, −K: nontransfected K62 cells.

Figure 5:
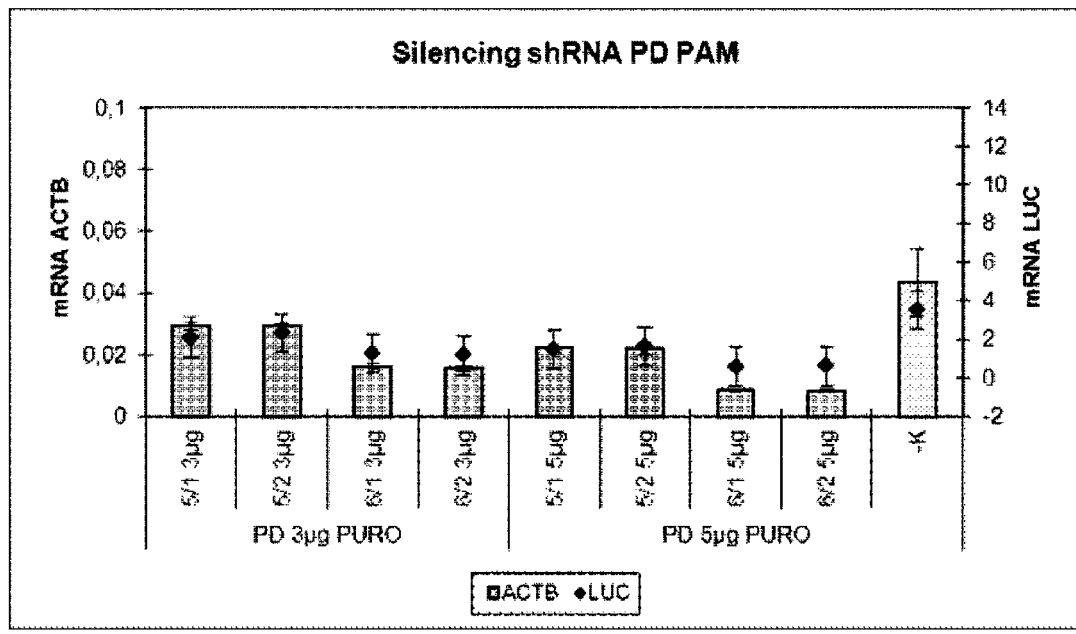

FIG. 5: Silencing of PAM mRNA using shRNA on the CHO K1 PD parental cell line. /1: parallel 1, /2: parallel 2, −K: nontransfected CHO K1 PD cells.

Figure 6:
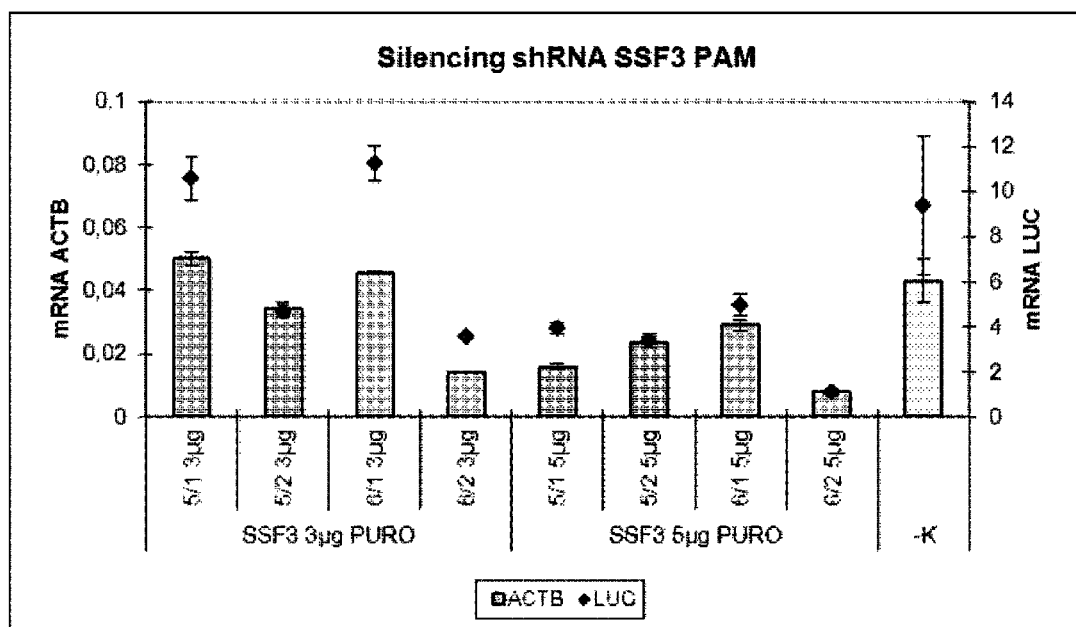

FIG. 6: Silencing of PAM mRNA using shRNA on CHO SSF3 parental cell line. /1: parallel 1, /2: parallel 2, −K: nontransfected CHO SSF3 cells.

The experiments shown in FIGS. 3-6 were designed to evaluate the mRNA expression level of PAM using different shRNAs and different concentrations of puromycin (PURO) on tested cell lines. The highest silencing effect was observed using sh6 (if used alone or in the mix with sh5) on all cell lines respectively. This was also proven by calculating % decrease in expression of PAM mRNA (Table 11) and using Student's t-Test (Table 12). Only a minor reduction of the expression level was observed using 5 μg/ml puromycin. Silencing of PAM was determined on mRNA and protein level respectively.

Figure 7:
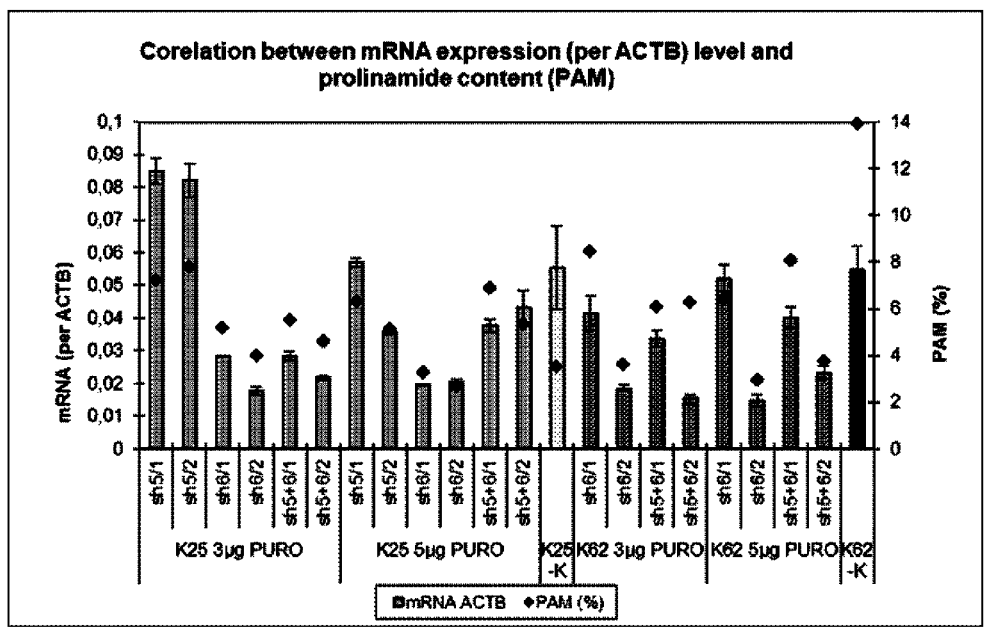

FIG. 7: Correlation between PAM mRNA expression level and mAb proline amide content. /1: parallel 1, /2: parallel 2, −K: nontransfected K25 and K62 cells.

Figure 8:
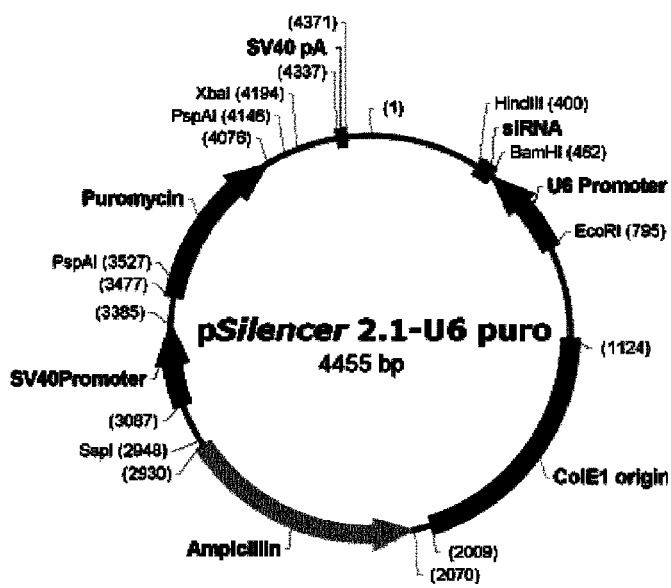

FIG. 8: Chart of pSilencer 2.1-U6 puro vector

FIG. 9: Reaction catalysed by peptidylglycine alpha-amidating monooxygenase (PAM). PAM is a multifunctional protein containing two enzymatic activities that act sequentially to catalyse the C-terminal truncation and alpha-amidation of peptides. peptidylglycine alpha-hydroxylating monooxygenase (PHM) catalyses the first step of the reaction (peptidylglycine (C-terminal)→peptidyl-α-hydrooxiglycine) and is dependent on copper (Cu), or copper ions, ascorbate, and molecular oxygen. The zinc dependent peptidylamido-glycolate lyase (PAL) catalyses the second step of the reaction (peptidyl-α-hydrooxiglycine→peptide-α-amide and glyoxylate). Figure taken from Prigge et al., Science (1997) 278, 1300-1305.

EXPERIMENTS 1. siRNA Based Gene Silencing

Chinese hamster ovary (CHO) cells are a cell line derived from the ovary of the Chinese hamster (*Cricetulus griseus*). They are often used in biological and medical research and commercially in the production of therapeutic proteins. For this reason, it was experimentally shown to reduce peptide amidation activity in a CHO cell line. The exact sequence of the enzyme responsible for proline amide formation in CHO cells is not published in the literature or public databases. The potential nucleotide sequences were extracted from a proprietary CHO EST database. On the basis of this sequence information, siRNAs were constructed, and their silencing effect was evaluated. Short hairpin RNAs (shRNAs) were constructed on the basis of siRNA results, and the gene suppression was evaluated on the mRNA and protein level.

After determination of the *C. griseus* peptidylglycine alpha-amidating monooxygenase nucleotide sequence (Table 1), 9 and 6 siRNA sequences were designed. The silencing effect was tested after transfection and cultivation of two CHO parental cell lines and two mAb producing CHO cell lines, one producing a product containing high and one with a low proline amide level, respectively. After cultivation, the PAM mRNA level was determined by qPCR and two silencers with the most potent effect were selected for shRNA design. After transfection of cells using shRNA and subsequent cell cultivation, both the mRNA and PAM level were analysed. Experimental details are presented below.

TABLE 1

PAM gene sequence extracted from a proprietary CHO EST database. PAM gene sequence extracted from a proprietary CHO EST database used for siRNA construction (SEQ ID No 1):

GGGAGTGCTCCTAAGCCAGGCCAGTTCAGTGTTCCTCACAGTTTGGCCCT

TGTGCCTCATTTGGACCAGTTGTGTGTGGCAGACAGGGAAAATGGCCGGA

TCCAATGTTTCAGAACTGACACCAAAGAATTTGTGAGAGAGATTAAACAT

GCGTCATTTGGGAGAAATGTATTCGCAATTTCATATATATCAGGTTTGCT

CTTTGCAGTAAATGGGAAGCCTTACTTTGGAGACCATGAACCTGTGCAAG

GCTTTGTGATGAACTTTTCCAGTGGGGAAATTATAGATGTCTTCAAGCCA

GTACGCAAGCACTTTGACATGCCTCACGATGTGGTTGCCTCTGACGATGG

GAATGTGTACATTGGAGACGCACACACGAACACGGTGTGGAAGTTCACCC

TGACTGAAAAAATGGAGCATCGATCGGTTAAAAAGGCAGGCATTGAGGCT

CAGGAAATCAAAGAAACCGAGGCAGTTGTTGAATCCAAAATGGAGAACAA

ACCCACCTCCTCAGAATTGCAGAAGATGCAAGAGAAACAGAAACTGATCA

AAGAGCCAGGTTCGGGAGTGCCCGTGGTTCTCATTACAACCCTTCTGGTT

ATTCCTGTGGTTGTCCTGCTGGCCATTGTCATGTTTATTCGGTGGAAAAA

ATCAAGGGCCTTTGGAGGAAAA siRNA and shRNA Design and Preparation

Respective design tools were utilised to design siRNA sequences against the peptidylglycine alpha-amidating monooxygenase (PAM) gene. On the basis of gene sequence siRNAs of different sequences and lengths were designed (9 by Invitrogen and 6 by Ambion) (Table 2). After siRNA evaluation, shRNAs were designed using Ambion's online design tool. Two complementary oligonucleotides for each shRNA were synthesised by Methabion (Table 3) and then annealed to generate double stranded oligonucleotides in house. Subsequently, the annealed oligonucleotides were cloned into the pSilencer 2.1-U6 puro vector (FIG. 8). DNA sequencing was performed to verify the sequence of the oligonucleotide insert.

TABLE 2

Nucleotide sequences of siRNAs

| Name | siRNA_Oligonucleotide | SEQ ID No |
|---|---|---|
| siRNA_1 | CAGUUGUGUGUGGCAGACAGGGAAA | 2 |
| siRNA_2 | CGGAUCCAAUGUUUCAGAACUGACA | 3 |
| siRNA_3 | CCAAUGUUUCAGAACUGACACCAAA | 4 |
| siRNA_4 | GAGAGAGAUUAAACAUGCGUCAUUU | 5 |
| siRNA_5 | CAUGCGUCAUUUGGGAGAAAUGUAU | 6 |
| siRNA_6 | UGGGAGAAAUGUAUUCGCAAUUUCA | 7 |
| siRNA_7 | GGGAGAAAUGUAUUCGCAAUUUCAU | 8 |
| siRNA_8 | CACACGAACACGGUGUGGAAGUUCA | 9 |
| siRNA_9 | CAAAGAAACCGAGGCAGUUGUUGAA | 10 |
| siRNA_1 | CAGUAAAUGGGAAGCCUUAUU | 11 |
| siRNA_2 | AGGCAGUUGUUGAAUCCAAUU | 12 |
| siRNA_3 | AACAGAAACUGAUCAAAGAUU | 13 |
| siRNA_4 | CAAGAGAAACAGAAACUGAUU | 14 |
| siRNA_5 | GAACUGACACCAAAGAAUUUU | 15 |
| siRNA_6 | UUUCAGAACUGACACCAAAUU | 16 |

TABLE 3

Nucleotide sequences of shRNAs

| Name | shRNA_Sense Strand Oligonucleotide | SEQ ID No | shRNA_Antisense Strand Oligonucleotide | SEQ ID No |
|---|---|---|---|---|
| SH5_HLPAM | 5'GATCCGAACTGACACCAAAGAATTCTCAAGAGAAATTCTTTGGTGTCAGTTCTGTTTTTTGGAAA-3' | 17 | 5'AGCTTTTCCAAAAAACAGAACTGACACCAAAGAATTTCTCTTGAGAATTCTTTGGTGTCAGTTCG-3' | 19 |
| SH6_HLPAM | 5'GATCCGTTTCAGAACTGACACCAAACTCAAGAGATTTGGTGTCAGTTCTGAAACATTTTTGGAAA-3' | 18 | 5'AGCTTTTCCAAAAAATGTTTCAGAACTGACACCAAATCTCTTGAGTTTGGTGTCAGTTCTGAAACG-3' | 20 |

Reconstitution of siRNA siRNAs were reconstituted in DEPC water to final 40 μM concentration. 30 pmol of siRNA were used for each parallel nucleofection.

Cloning Hairpin siRNA Inserts into pSilencer Vector

Two complementary oligonucleotides for each shRNA were annealed to generate double stranded oligonucleotides. Subsequently, annealed oligonucleotides were cloned into the pSilencer 2.1-U6 puro vector using BamHI and HindIII restriction sites. The whole procedure was performed as follows:

1. Dissolve the hairpin siRNA template oligonucleotides in approximately 100 µl of nuclease-free water.

2. Dilute the oligonucleotides to approx. 1 µg/µl in TE.

3. Assemble the 50 µl annealing mixture as follows (Table 4):

TABLE 4

Annealing of siRNAs

| Amount | Component |
| --- | --- |
| 2 µl | sense siRNA template oligonucleotide |
| 2 µl | antisense siRNA template oligonucleotide |
| 46 µl | 1 × DNA Annealing solution |

4. Heat mixture to 90° C. for 3 min, then place in a 37° C. incubator and incubate 1 hr.

5. Dilute 5 µl of the annealed hairpin siRNA template insert with 45 µl nuclease free water to a final concentration of 8 ng/µl.

6. Set up two 10 µl ligation reactions; a plus insert ligation and a minus insert negative control.

To each tube, add the following reagents (Table 5):

TABLE 5

Ligation reactions

| Plus insert | Minus insert | Component |
| --- | --- | --- |
| 1 µl | — | Diluted annealed siRNA insert |
| — | 1 µl | 1 × DNA Annealing solution |
| 6 µl | 6 µl | Nuclease free water |
| 1 µl | 1 µl | 10 × T4 DNA ligase buffer |
| 1 µl | 1 µl | pSilencer vector |
| 1 µl | 1 µl | T4 DNA ligase (5 U/µl) |

7. Incubate at 16° C. overnight.

8. For the transformation use pGEM-T Easy Vector System (Promega, Cat. No.: A13801):

a) Place the *E. coli* JM109 competent cells in an ice bath until thawed.

b) Transfer 50 µl of cells to the ligation reaction tubes and add 3 µl of ligation reaction to each tube. Gently flick the tubes and incubate for 20 min.

c) Heat-shock the cells for 50 s in water bath at 42° C. Immediately return the tubes to ice for 2 min.

d) Add 950 µl of LB medium to the transformation reactions and incubate for 1.5 hr at 37° C. with shaking (225 rpm).

e) Plate 100 µl of each transformation culture onto LB/ampicillin plates and incubate overnight at 37° C.

f) To identify clones with the siRNA template insert pick clones, isolate plasmid DNA, and digest with BamHI and HindIII, to confirm the presence of the ~65 bp siRNA template insert.

9. Sequence the insert using following sequencing primers (Table 6):

TABLE 6

Sequencing primers

| Forward sequencing primer (SEQ ID No 21) | Reverse sequencing primer (SEQ ID No 22) |
| --- | --- |
| 5'-AGGCGATTAAGTTGGGTA-3' | 5'-TAATACGACTCACTATAGGG-3' |

After isolation and verification of the shRNA expression constructs, they were linearised using the single cutter restriction endonuclease Sspl (AAT/ATT). Maximal 50 µg of plasmid DNA per reaction was digested using the Sspl enzyme at 3 U/µg DNA (New England Biolabs, Cat. No.: R0132L). An appropriate amount of 10× reaction buffer and H$_2$O was added to the reaction. The reaction was incubated at 37° C. for 3 hours. After digestion, DNA precipitation was performed under aseptic conditions in a laminar air-flow cabinet as described in the protocol below:

1. Add 1 volume of isopropanol (300 µl)
2. Vortex thoroughly
3. Centrifuge 30 min at 21,000 g at 4° C.
4. Discard the supernatant
5. Add carefully 1 volume of sterile, ice cold 70% ethanol
6. Centrifuge 1 min at max speed, at 4° C.
7. Discard the supernatant
8. Air dry pellet at RT for 5-30 min. (in laminar)
9. Resuspend DNA in 50 µl sterile water.

Next, purity (O.D. 260/280 nm) and the concentration of linear DNA were determined using the NanoDrop ND-1000.

Host Cells

Four different cell lines were used during the study (parental CHO K1 PD and SSF3 cell lines and two mAb producing clones, K25 and K62). The CHO K1 PD cell line is a subpopulation of the CHO K1 cell line which originates from ATCC (Cat. No. CCL-61.3). The original cell line was adapted to serum free suspension culture and underwent 3 successive rounds of selection at increasingly dilute seeding densities to improve the frequency of serum-free subcloning in DM122 medium. The CHO SSF3 cell line is a serum free adapted cell line from DUKXB1. DUKXB1 was derived from CHO K1 cells. Both functional dhfr alleles were sequentially inactivated in CHO K1. However, the results showed that one of alleles is not inactivated irreversibly. Continuous serum free culture unexpectedly induced expression of low dihydrofolate reductase activity in the originally dihydrofolate reductase deficient (dhfr) CHO cells.

K25 and K62 were prepared by transfection of the SSF3 parental cells with the pBW2017 plasmid vector. It was shown in previous experiments that both clones are expressing a mAb product which contains undesired proline amide structures. K25 and K62 were included in silencing experiments since the respective mAb products contained two extreme values of proline amide, i.e. a low proline amide content on the mAb produced by K25 (4%) and a high proline amide content on the mAb produced by K62 (14%).

Nucleofection

The Amaxa nucleofection system was used for cell transfection (Nucleofector kit V, Cat. No.: VCA-1003). Not more than 5 pools are transfected at once, to enable sufficient time for all necessary cell manipulations. A detailed protocol is described below:

1. At the time of transfection, cells should be up to 2E6/ml with viability≥90%.

2. 5E6 cells are used per nucleofection.
3. Count cells and centrifuge at 90×g, 10 min, RT in 50 ml centrifuge tube.
4. Carefully remove the rest of the medium and resuspend the cell pellet in solution V (100 µl per transfection)
5. Add DNA (30 pmol siRNA/nucleofection or 3 µg/nucleofection shRNA) and mix gently.
6. Add 100 µl cell suspension mixed with DNA into the transfection cuvette, place it in an Amaxa Nucleofector device.
7. Transfect the cells via nucleofection using Amaxa program U 23
8. Add some growth medium into the cuvette and transfer the cells carefully in a 125 ml shake flask with 20 ml medium. Rinse the cuvette 1-2× with fresh medium and add it to the shake flask. Incubate the cells for 24-48 h in a shaker (120 rpm), at 37° C., 10% $CO_2$.

Growth Medium

CHO K1 PD cells were cultivated in a suitable medium for culturing mammalian cells, such as DM122 growth medium supplemented with 8 mM L-glutamine (Sigma, Cat. No.: G7513). CHO SSF3 cells were cultivated in DM122 growth medium supplemented with 8 mM L-glutamine (Sigma, Cat. No.: G7513) and 1 mg/L insulin (Millipore, Cat. No.: 10131-027). K25 and K62 were cultivated in DM122 growth medium supplemented with 8 mM L-glutamine (Sigma, Cat. No.: G7513), 1 mg/L insulin (Millipore, Cat. No.: 10131-027) and 150 nM methotrexate (methotrexate hydrate, Sigma, Cat. No.: M8407). Cell selection steps were performed in the same medium additionally supplemented with 3 µg/ml and subsequently 5 µg/ml of puromycin (Gibco, Cat. No.: A11138-02).

Thawing/Freezing of Cells

Vials were thawed in 70% ethanol at 37° C. Cells were drop-wise inoculated directly into 250 ml shake flasks containing 50 ml pre-warmed medium at an initial cell density of cca. 1E5 viable cells per ml. Cells were cultured at 37° C., 10% $CO_2$, 120 rpm. Cells were frozen in exponential growth phase at a viability>90%. 5-10E6 viable cells per vial were frozen in conditioned medium containing 7.5% DMSO. First the cell culture was centrifuged at 180 g, 5 min, RT, redundant supernatant was discarded. Subsequently DMSO was added to a final concentration of 7.5%. Cell pellets were gently resuspended. Cryo-vials were filled with 1 ml of cell suspension and transferred into a −80° C. deep freezer in a Mr. Frosty cryo box. Within 1 month the frozen vials were transferred into a liquid nitrogen container.

Culture and Handling of Cells

For siRNA experiments CHO K1 PD cells were transfected with siRNAs using nucleofection and cultivated for four days. On day four, cell pellets were collected for qPCR analysis. For shRNA experiments all four cell lines (CHO K1 PD, CHO SSF3, K25 and K62) were transfected with shRNAs using nucleofection. Cells were split on a 2-2-3-day schedule at 2-3E5 cells per ml in the appropriate pre-warmed medium to maintain exponential cell growth. After reaching the appropriate cell density and viability cells were divided and further processed in four separate steps:
1. samples were collected for qPCR (cell pellets)
2. a 10 day batch containing 3 µg/ml of puromycin was inoculated (after 10 days supernatants were collected for CEX analysis)
3. 3 cell vials of each cell culture were frozen
4. cells were further cultivated in the medium containing 5 µg/ml of puromycin.

After reaching the appropriate cell density and viability using 5 µg/ml of puromycin steps 1, 2, and 3 were repeated.

Cells were cultivated in 125 ml shake flasks. Incubation conditions: 37° C., 90-110 rpm for 125 and 250 ml shake flasks and 10% $CO_2$ for DM122 medium Puromycin Selection Antibiotic selection using puromycin was the first selection step after transfection. All transfected pools were selected using puromycin at a final concentration of 3 mg/ml. Puromycin was added to the cell culture 2 days after transfection when cell viability exceeded 60%. After each pool has reached at least 85% cell viability we proceeded with the selection using 5 mg/ml of puromycin.

RNA Isolation and cDNA Synthesis 10 ng of luciferase RNA (Promega, Cat. No.: L4561) was added to 5E6 cells prior to RNA isolation. Total RNA (totRNA) was isolated using RNeasy Mini Kit (Qiagen, Cat. No.: 74104) on the automated workstation QIAcube. After isolation, the totRNA concentration was measured on Nano-Drop. Subsequently, DNase I (Ambion, Cat. No.: AM1906) was added to 5 µg of totRNA (Table 7) and incubated (25 min 37° C., 10 min 75° C.). After DNase treatment RNA was transcribed into cDNA using SuperScript VILO kit (Invitrogen, Cat. No.: 11754-050).

TABLE 7

| DNase I treatment and cDNA synthesis | | | |
|---|---|---|---|
| DNase treatment | | cDNA synthesis | |
| 5 µg totRNA | X µL | DNase treated totRNA | 5 µL |
| 10 × DNaseI Buffer | 5 µL | 5 × VILO reaction mix | 4 µL |
| DNaseI | 5 µg | 10 × superscript enzyme | 2 µL |
| NF water | up to 50 µL | DEPC water | 9 µL | qPcr

A qPCR method based on TaqMan chemistry was used for mRNA level determination (TaqMan MasterMix, Applied Biosystems, Cat. No.: 4326708 and Assay by design, Applied Biosystems, Cat. No.: 4331348, see Table 8). PAM mRNA expression level was calculated using absolute quantification and was expressed as the number of mRNA transcripts per cell as well as per reference gene ACTB (β-actin). In case of calculation per ACTB gene a standard curve was constructed using isolated genomic DNA and was used for determination of ACTB mRNA copy number. The ratio between mRNA of PAM and ACTB was determined. When the mRNA copy number was calculated per cell, a standard curve was constructed using luciferase DNA and the mRNA copy number for luciferase was determined. The ratio between the mRNA of PAM and LUC was then calculated, and the mRNA level of PAM per cell was determined (see FIGS. 1-6)

TABLE 8

| Nucleotide sequences of qPCR primers and probes | | | | | | |
|---|---|---|---|---|---|---|
| | Forward primer | SEQ ID No | Reverse primer | SEQ ID No | Probe | SEQ ID No |
| PAM | GGCCGGAT CCAATGTT TCAGAA | 23 | TCCCAAATGA CGCATGTTTA ATCTCT | 26 | FAM- CTGACACCAA AGAATTT | 29 |
| ACTB | AGCCACGC TCGGTCAG | 24 | CATCCTGCGT CTGGACCT | 27 | FAM- CCGGGACCTG ACAGACT | 30 |

TABLE 8-continued

Nucleotide sequences of qPCR primers and probes

|  | Forward primer | SEQ ID No | Reverse primer | SEQ ID No | Probe | SEQ ID No |
|---|---|---|---|---|---|---|
| LUC | CTGATTTT TCTTGCGT CGAGTTT | 25 | GAGTTGTGTT TGTGGACGAA GTAC | 28 | FAM-TCCGGTAAGA CCTTTCG | 31 |

Cation Exchange Chromatography (CEX)

Protein A purified mAbs were analysed by CEX using an analytical HPLC chromatographic system. Using this method Lys and proline amide are eluted in the same peak. The amount of proline amide was further determined by product C-terminus treatment with carboxypeptidase. Followed by the same CEX analysis, the remaining peak presents the amount of proline amide.

Experimental Results

The goal of this study was to evaluate the silencing effect on PAM gene by siRNA and shRNA. Silencing of PAM was determined on mRNA and protein level respectively. CHO K1 PD cells were transfected by siRNAs to determine the sequence with the most potent silencing effect (FIGS. 1-2 and Tables 9-10).

TABLE 9

Silencing effect in % difference when calculated per ACTB or per LUC.

|  | Silencing [%] per ACTB | Silencing [%] per LUC |
|---|---|---|
| siRNA Invitrogen | | |
| si1 | 60.5 | 50.2 |
| si2 | 79.7 | 78.4 |
| si3 | 85.7 | 83.8 |
| si4 | 68.0 | 64.7 |
| si5 | 78.0 | 73.3 |
| si6 | 89.6 | 89.1 |
| si7 | 87.9 | 85.6 |
| si8 | 85.5 | 83.9 |
| si9 | 55.0 | 51.8 |
| siRNA Ambion | | |
| si1 | 31.9 | 32.1 |
| si2 | 56.1 | 62.4 |
| si3 | 45.2 | 50.6 |
| si4 | 52.0 | 56.5 |
| si5 | 73.2 | 74.1 |
| si6 | 71.9 | 74.0 |

TABLE 10

Student's t-Test

|  | p-value | p-value |
|---|---|---|
| siRNA Invitrogen | | |
| si1 | 0.11 | 0.09 |
| si2 | 0.06 | 0.11 |
| si3 | 0.06 | 0.03 |
| si4 | 0.09 | 0.06 |
| si5 | 0.07 | 0.04 |
| si6 | 0.05 | 0.03 |
| si7 | 0.05 | 0.03 |
| si8 | 0.06 | 0.03 |
| si9 | 0.13 | 0.08 |
| siRNA Ambion | | |
| si1 | 0.58 | 0.16 |
| si2 | 0.32 | 0.04 |
| si3 | 0.44 | 0.03 |
| si4 | 0.36 | 0.03 |
| si5 | 0.22 | 0.01 |
| si6 | 0.23 | 0.02 |

From the results shown above (FIGS. 1-2 and Table 9) we can conclude that there is up to 90% decrease in expression of PAM mRNA using Invitrogen siRNAs and up to 75% decrease using Ambion siRNAs. Student's t-Test (Table 10) was performed to determine which siRNA's differ significantly from the negative control. The results show the same observations as obtained after calculation percentual difference (lower p-value presents greater difference in expression in comparison to negative control). On the basis of these results two siRNA sequences were selected and shRNA vectors were constructed (si5, si6 for PAM). Due to the shRNA design limitations only sequences from Ambion's siRNAs were used for shRNA construction. To evaluate the silencing of PAM two parental cell lines CHO K1 PD and SSF3 and two mAb producing clones (K25 with low and K62 with high content of proline amide on the product) were transfected with each of the two shRNAs respectively and with the mix of both. Selection of the transfected cells was performed with two different concentrations of puromycin consecutively (FIGS. 3-6). Silencing of PAM was further on evaluated on the protein level by CEX analysis of the produced mAb and the correlation to the mRNA level was determined (FIG. 7).

The results on FIGS. 3-6 show the mRNA expression level of PAM using different shRNAs and different concentrations of puromycin (PURO) on tested cell lines. The highest silencing effect was observed using sh6 (if used alone or in the mix with sh5) on all cell lines respectively. This was also proven by calculating % decrease in expression of PAM mRNA (Table 11) and using Student's t-Test (Table 12). Only a minor reduction of the expression level was observed using 5 µg/ml puromycin.

TABLE 11

Silencing effect in % difference when calculated per ACTB or pre LUC

|  |  | Silencing [%] per ACTB | Silencing [%] per LUC |
|---|---|---|---|
| K25 3 µg PURO | sh5/1 | −50.8 | −18.8 |
|  | sh6/1 | 58.6 | 56.9 |
|  | sh5 + 6/1 | 45.2 | 48.6 |
| K25 5 µg PURO | sh5/1 | 16.2 | 47.0 |
|  | sh6/1 | 63.7 | 76.6 |
|  | sh5 + 6/1 | 27.0 | 45.9 |
| PD 3 µg PURO | sh5 | 32.1 | 37.7 |
|  | sh6 | 63.2 | 65.1 |
| PD 5 µg PURO | sh5 | 48.9 | 55.7 |
|  | sh6 | 80.3 | 83.1 |
| K62 3 µg PURO | sh6 | 44.9 | 38.8 |
|  | sh5 + 6 | 55.1 | 66.5 |
| K62 5 µg PURO | sh6 | 38.8 | 52.0 |
|  | sh5 + 6 | 41.9 | 47.3 |
| SSF3 3 µg PURO | sh5 | 2.0 | 18.5 |
|  | sh6 | 30.5 | 20.8 |

TABLE 11-continued

Silencing effect in % difference when calculated per ACTB or pre LUC

|  |  | Silencing [%] per ACTB | Silencing [%] per LUC |
|---|---|---|---|
| SSF3 5 µg | sh5 | 38.8 | 55.4 |
| PURO | sh6 | 56.8 | 67.9 |

TABLE 12

Student's t-Test

|  |  | Silencing [%] per ACTB | Silencing [%] per LUC |
|---|---|---|---|
| K25 3 µg | sh5/1 | 0.06 | 0.67 |
| PURO | sh6/1 | 0.04 | 0.27 |
|  | sh5 + 6/1 | 0.04 | 0.33 |
| K25 5 µg | sh5/1 | 0.56 | 0.35 |
| PURO | sh6/1 | 0.04 | 0.18 |
|  | sh5 + 6/1 | 0.17 | 0.35 |
| PD 3 µg | sh5 | 0.17 | 0.01 |
| PURO | sh6 | 0.03 | 0.00 |
| PD 5 µg | sh5 | 0.07 | 0.00 |
| PURO | sh6 | 0.01 | 0.00 |
| K62 3 µg | sh5 | 0.02 | 0.27 |
| PURO | sh6 | 0.01 | 0.01 |
| K62 5 µg | sh5 | 0.09 | 0.24 |
| PURO | sh6 | 0.02 | 0.05 |
| SSF3 3 µg | sh5 | 0.94 | 0.68 |
| PURO | sh6 | 0.51 | 0.70 |
| SSF3 5 µg | sh5 | 0.06 | 0.12 |
| PURO | sh6 | 0.17 | 0.16 |

The results in FIG. 7 show a correlation between mRNA and PAM modified mAb. This correlation vas also shown by calculating Pearson's function (Pearson's correlation coefficient was determined to be 0.55).

2. Targeted Gene Knockout in CHO Cells by Using Zinc Finger Nucleases (ZFNs)

ZFNs can be designed to target a chosen locus with high specificity. Upon transient expression of these nucleases, the target gene is first cleaved by the ZFNs and then repaired by a natural—but imperfect—DNA repair process, nonhomologous end joining. This often results in the generation of mutant (null) alleles. Such approach is for example described in Santiago et al., 2008 ("Targeted gene knockout in mammalian cells by using engineered zinc-finger nucleases", PNAS Apr. 15, 2008 vol. 105 no. 15).

Site-specific zinc-finger nucleases which target the PAM gene locus are designed and screened in vitro for DNA binding to their target sites. The nuclease function of ZFNs is conferred by the catalytic domain of the endonuclease FokI, which is linked to the DNA-binding zinc-finger proteins.

Plasmids expressing each pair of ZFNs are transfected into CHO cells. The frequency of ZFN-mediated disruption at the target site in each pool of cells is determined by using a CEL-I nuclease.

PAM$^{-/-}$ cell lines are generated by transfecting CHO cells with a ZFN pair and then performing a cloning step (e.g., by limiting dilution, ClonePix™ [Molecular Devices Ltd., UK] or flow cytometry sorting) to obtain single-cell derived PAM-deficient cell lines. After cloning, isolates are analyzed for PAM gene disruption, using the CEL-I assay or qPCR analysis. The exact sequence of the mutant alleles in each cell line, and thus the genotype, is determined by PCR-amplifying the target locus and cloning the PCR product, or by using one of the available second generation sequencing technologies.

3. Gene Targeting with TALENs

TALENs are novel fusion proteins that consist of assembled DNA-binding motifs coupled to FokI nuclease. The DNA-binding motifs come from proteins secreted by plant pathogens in the bacterial genus *Xanthomonas*.

Assembly of a custom TALEN, or TAL effector construct, is described, e.g., in Cermak et al., 2011 ("Efficient design and assembly of custom TALEN and other TAL effector-based constructs for DNA targeting"; Nucl. Acids Res. 39 (12)), and involves two steps: (i) assembly of repeat modules into intermediary arrays of 1-10 repeats and (ii) joining of the intermediary arrays into a backbone to make the final construct. Details of this process are described in Cermak et al. 2011

Software to design TALENs is available for use as an online tool (TAL Effector-Nucleotide Targeter, TALE-NT; http://boglabx.plp.iastate.edu/TALENT/). The tool provides a window to input DNA sequences of the gene of interest to be targeted, e.g., the PAM gene. The software identifies sets of TALEN recognition sites between 15 and 30 bp in length and separated by a spacer. The default spacer lengths are 15 bp and 18-30 bp, but other lengths can be specified by the user. In addition, buttons allow users to exclude design guidelines individually.

One of the pairs of TALENs targeting the PAM gene is subcloned into the mammalian expression vector pCDNA3.1(–) (Invitrogen) using XhoI and AflII. These enzymes excise the entire TALEN from pTAL3 or pTAL4 and place the coding sequence under control of the CMV (cytomegalovirus) promoter. The resulting plasmids are introduced into HEK293T cells by transfection (e.g. by using Lipofectamine 2000 (Invitrogen) following the manufacturer's protocol). Cells are collected 72 h after transfection and genomic DNA isolated and digested with Hpy188I, which cuts in the spacer sequence of the TALEN target site. After digestion, a chromosomal fragment encompassing the target site is amplified by PCR. Subsequently, the PCR products are digested with Hpy188I and cloned into a TOPO TA vector (Invitrogen). Independent clones containing the full-length PCR product are sequenced to evaluate mutations at the cleavage site.

What is claimed is:

1. A cell transformed to express a heterologous protein having reduced peptide amidation, wherein the expression of a gene or translation of a gene encoding an enzyme catalyzing peptide a-amidation in the cell is inhibited or reduced.

2. The cell of claim 1, wherein the cell is a eukaryotic cell.

3. The cell of claim 1, wherein the cell is an animal cell and/or a plant cell.

4. The cell of claim 1, wherein the cell is a mammalian cell.

5. The cell of claim 1, wherein the cell is a recombinant cell.

6. The cell of claim 1, wherein the cell is a Baby hamster Kidney cell, a Chinese hamster ovary cell, a mouse myeloma cell, a human embryonic kidney cell, a human-retina-derived cell, or an amniocyte cell.

7. The cell of claim 1, wherein the enzyme catalysing peptide amidation is peptidylglycine alpha-amidating monooxygenase (PAM).

8. The cell of claim 1, wherein the enzyme catalysing peptide a-amidation catalyses the formation of C-terminal proline amide residues.

9. The cell of claim 1, wherein the translation of the gene encoding for said enzyme catalysing peptide a-amidation is inhibited, or reduced, by means of RNA interference (RNAi).

10. The cell of claim 1, wherein the cell comprises an siRNA or shRNA molecule comprising nucleotide sequences that are complementary to a portion of a peptidylglycine alpha-amidating monoxygenase (PAM) gene.

11. The cell of claim 10, wherein the shRNA nucleotide sequences are SEQ ID NOs: 17 and 19 or SEQ ID NOs: 18 and 20.

12. The cell of claim 10, wherein the siRNA or shRNA is in an expression vector.

13. A method for the recombinant production of a heterologous protein having reduced peptide amidation, wherein said method comprises:

a) transforming a cell express a heterologous protein, wherein the expression of a gene or translation of a gene encoding an enzyme catalyzing peptide a-amidation in the cell is inhibited or reduced, and b) culturing said cell under conditions to express said heterologous protein.

14. The method of claim 13, wherein the cell is a eukaryotic cell.

15. The method of claim 13, wherein the cell is an animal cell and/or a plant cell.

16. The method of claim 13, wherein the cell is a mammalian cell.

17. The method of claim 13, wherein the cell is a recombinant cell.

18. The method of claim 13, wherein the cell is a Baby hamster Kidney cell, a Chinese hamster ovary cell, a mouse myeloma cell, a human embryonic kidney cell, a human-retina-derived cell, or an amniocyte cell.

19. The method of claim 13, wherein the enzyme catalysing peptide amidation is peptidylglycine alpha-amidating monooxygenase (PAM).

20. The method of claim 13, wherein the enzyme catalysing peptide a-amidation catalyses the formation of C-terminal proline amide residues.

21. The method of claim 13, wherein the translation of the gene encoding for said enzyme catalysing peptide a-amidation is inhibited, or reduced, by means of RNA interference (RNAi).

22. The method of claim 13, wherein the cell comprises an siRNA or shRNA molecule comprising nucleotide sequences that are complementary to a portion of a peptidylglycine alpha-amidating monooxygenase (PAM) gene.

23. The cell of claim 22, wherein the shRNA nucleotide sequences are SEQ ID NOs: 17 and 19 or SEQ ID NOs: 18 and 20.

24. The cell of claim 22, wherein the siRNA or shRNA is in an expression vector.

* * * * *